(12) United States Patent
Motzer et al.

(10) Patent No.: US 10,288,585 B2
(45) Date of Patent: *May 14, 2019

(54) VARIABLE RADIUS INSPECTION USING SWEEPING LINEAR ARRAY

(71) Applicant: The Boeing Company, Chicago, IL (US)

(72) Inventors: William P. Motzer, Seattle, WA (US); James C. Kennedy, Renton, WA (US); Steven Ray Walton, Wilkeson, WA (US); James J. Troy, Issaquah, WA (US)

(73) Assignee: The Boeing Company, Chicago, IL (US)

( * ) Notice: Subject to any disclaimer, the term of this patent is extended or adjusted under 35 U.S.C. 154(b) by 185 days.

This patent is subject to a terminal disclaimer.

(21) Appl. No.: 14/869,170

(22) Filed: Sep. 29, 2015

(65) Prior Publication Data

US 2016/0274066 A1    Sep. 22, 2016

Related U.S. Application Data

(62) Division of application No. 13/466,285, filed on May 8, 2012, now Pat. No. 9,176,099.

(51) Int. Cl.
*G01N 29/26* (2006.01)
*G01N 29/04* (2006.01)
(Continued)

(52) U.S. Cl.
CPC ......... *G01N 29/265* (2013.01); *G01N 29/221* (2013.01); *G01N 29/225* (2013.01);
(Continued)

(58) Field of Classification Search
CPC .. G01N 29/265; G01N 29/221; G01N 29/225; G01N 2291/0231; G01N 2291/2638
(Continued)

(56) References Cited

U.S. PATENT DOCUMENTS 4,169,758 A  10/1979  Blackstone et al.
4,399,822 A   8/1983  Theumer
(Continued)

FOREIGN PATENT DOCUMENTS

DE    2733946 A1    2/1979
JP     019763 A  *  1/1990

OTHER PUBLICATIONS

Extended European Search Report, Aug. 1, 2013, European Patent Application No. 13164124.3 (European counterpart of the parent of the instant divisional application).

*Primary Examiner* — Helen C Kwok
*Assistant Examiner* — Nashmiya S Fayyaz
(74) *Attorney, Agent, or Firm* — Ostrager Chong Flaherty & Broitman P.C.

(57) ABSTRACT

Method and apparatus for enabling ultrasonic inspection of a changing, insufficiently defined or unknown shape (e.g., a variable radius or a noncircular radius caused by the use of soft tooling) at a rate that meets production requirements. The apparatus comprises a linear ultrasonic array (i.e., sensor) incorporated in a toppler, which in turn is slidably supported by an oscillating sensor mechanism carried by a traveling trailer vehicle. As a result of this arrangement, the sensor can undergo a back-and-forth sweeping motion coupled with motion along the spar radius. The sensor is further able to displace radially relative to a sweep pivot axis and rotate (hereinafter "topple") about a topple pivot axis. In this manner, the orientation of the sensor can adjust to the contour of the inspected surface as the sensor scans.

18 Claims, 13 Drawing Sheets

(51) Int. Cl.
*G01N 29/265* (2006.01)
*G01N 29/22* (2006.01)

(52) U.S. Cl.
CPC ............... *G01N 2291/0231* (2013.01); *G01N 2291/2638* (2013.01)

(58) Field of Classification Search
USPC ..................... 73/618, 622, 620, 619, 866.5
See application file for complete search history.

(56) References Cited

U.S. PATENT DOCUMENTS

| | | |
|---|---|---|
| 4,807,476 A | 2/1989 | Cook et al. |
| 6,722,202 B1 | 4/2004 | Kennedy et al. |
| 6,993,971 B2 | 2/2006 | Bossi et al. |
| 7,231,826 B2 | 6/2007 | Bossi et al. |
| 7,249,512 B2 | 7/2007 | Kennedy et al. |
| 7,263,889 B2 | 9/2007 | Kennedy et al. |
| 7,484,413 B2 | 2/2009 | Georgeson et al. |
| 7,685,726 B2 | 3/2010 | Fuchs et al. |
| 8,678,121 B2 | 3/2014 | Troy et al. |
| 8,763,462 B1 | 7/2014 | Fetzer et al. |
| 2005/0132811 A1 | 6/2005 | Mueller |
| 2006/0055399 A1 | 3/2006 | Georgeson et al. |
| 2006/0107775 A1 | 5/2006 | Wright et al. |
| 2006/0222138 A1 | 10/2006 | Shimamura et al. |
| 2007/0006657 A1 | 1/2007 | Kennedy et al. |
| 2009/0064787 A1 | 3/2009 | Kennedy et al. |
| 2010/0095775 A1 | 4/2010 | Sarr et al. |

\* cited by examiner

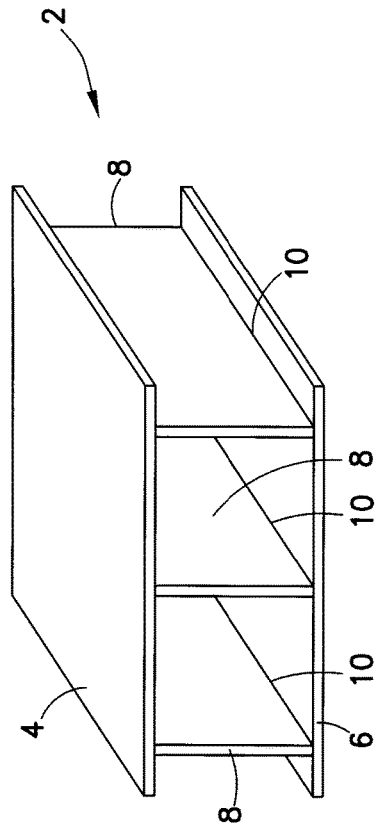
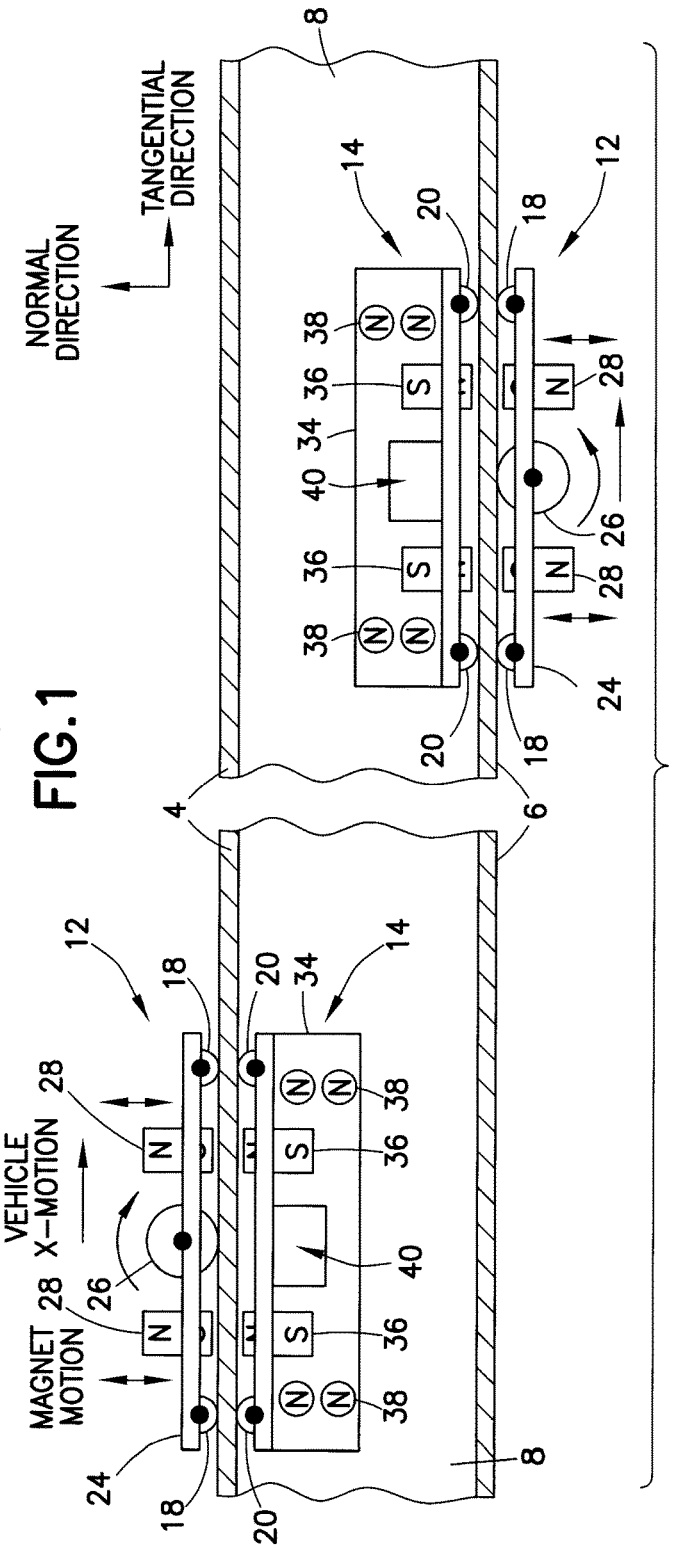
FIG. 1
FIG. 2

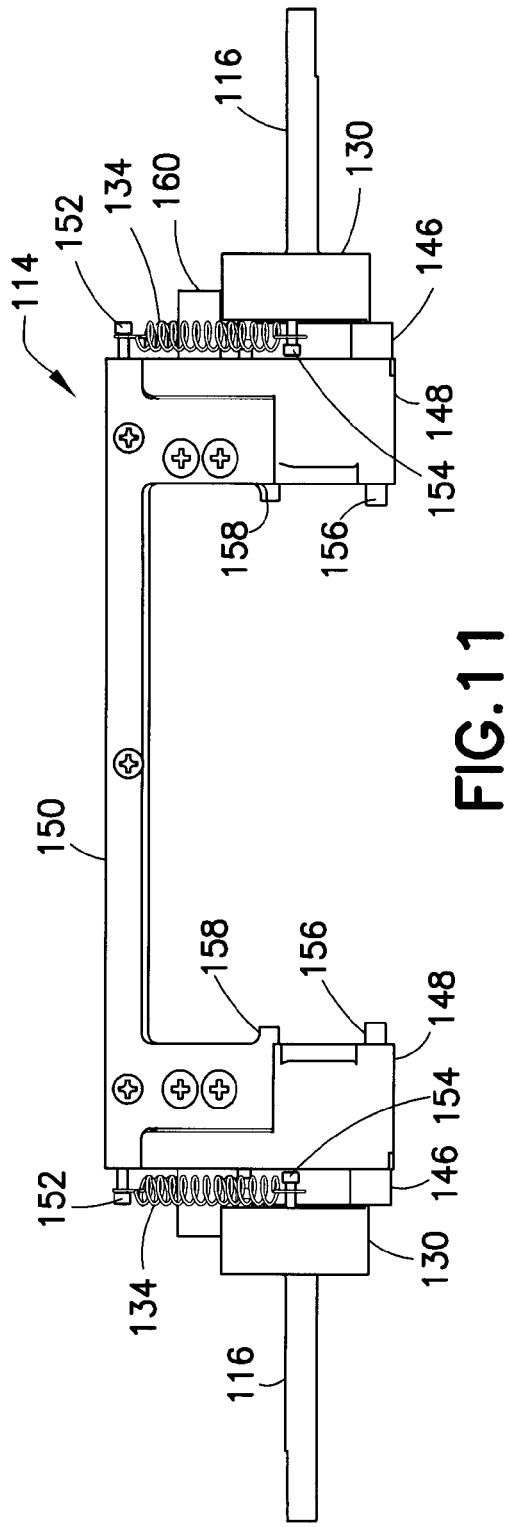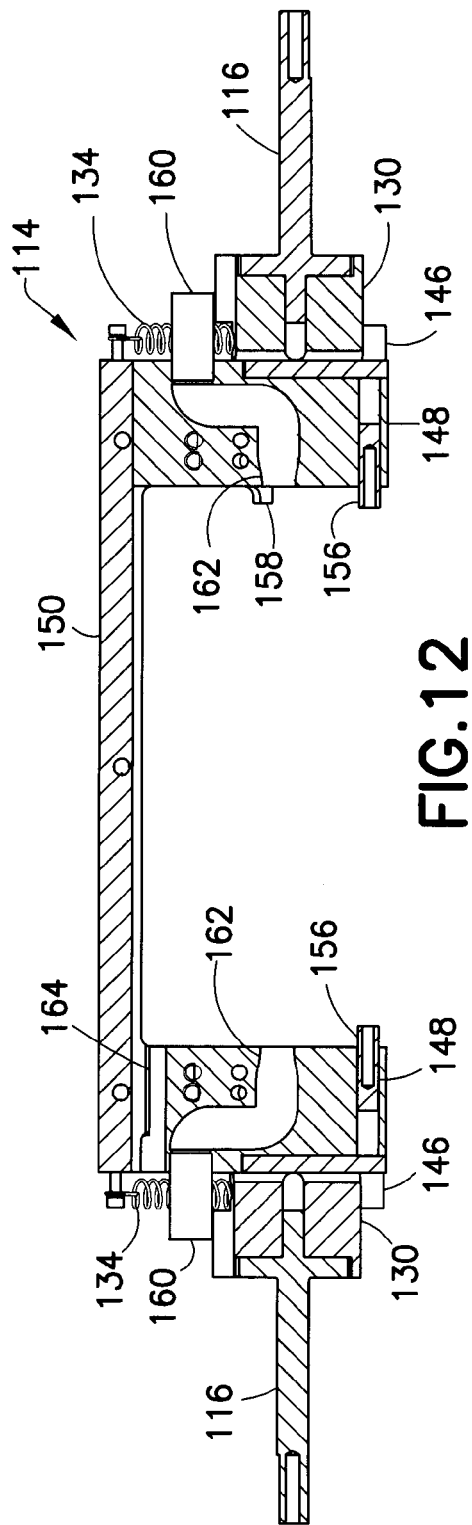

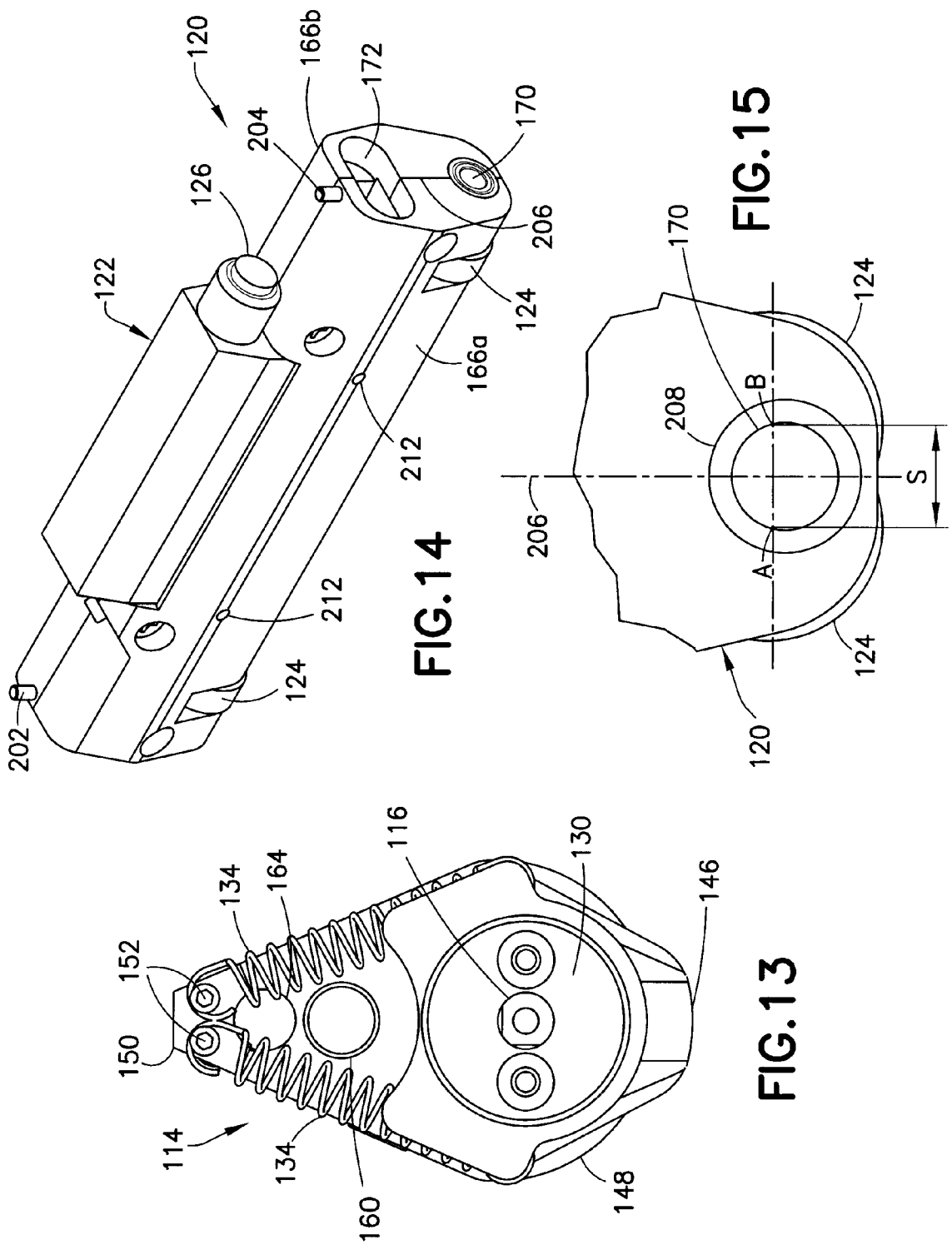

VARIABLE RADIUS INSPECTION USING SWEEPING LINEAR ARRAY

RELATED PATENT APPLICATION

This application is a divisional of and claims priority from U.S. patent application Ser. No. 13/466,285 filed on May 8, 2012.

BACKGROUND

This disclosure generally relates to inspection equipment and methods, and deals more particularly with methods and apparatus for inspecting a corner radius of a structure, especially a structure made of composite material.

A variety of elongated composite structures may have relatively confined internal cavities that require inspection in order to assure that the structure meets production and/or performance specifications. Conventional composite structure cured with hard tooling results in composite radii that are well defined and repeatable. In contrast, the composite radii formed using soft tooling are not always well defined and may vary from part to part. In some cases, dimensional or contour variations may be greater than those that would result from using hard tooling. These larger variations make reliable inspection more difficult. In view of the deviation from circularity of soft-tooled composite radii, the term "radius" as used hereinafter should be construed non-strictly to include non-circular profiles.

Critical composite structure in aerospace and potentially in applications outside aerospace must be inspected to required specifications to ensure structural integrity. Inspecting soft-tooled composite structures presents distinct yet interrelated challenges. Critical inspection areas include the radii. Moreover, such soft-tooled "radii" must be inspected in a production environment. For a production inspection, the inspection rate must be sufficient to meet the part production rate.

For ultrasonic inspection of composite structures, the sound beam should ideally enter at 90 degrees to the local surface of the composite part being inspected. If it does not enter at 90 degrees, it will be refracted off normal and a return echo from any possible internal structure or anomaly will not be possible. Traditionally a 90-degree entry angle is maintained by holding a sensor array at a precisely fixed position in space relative to the surface. While this works well for known surfaces, such as flat or cylindrical surfaces of a given, fixed radius and circular shape, it does not work at all for surfaces which are, for example, parabolic, irregular, or of varying radius of not-necessarily-cylindrical cross section. Traditional methods of interrogating such a radius with ultrasound fail to keep the sound path sufficiently perpendicular over the entire inspection area. The result is that traditional ultrasonic inspection methods that meet the required production rate do not work.

Accordingly, there is a need for methods and apparatus for inspecting composite structures having internal cavities that allow inspection of soft-tooled radii from inside the cavity at an inspection rate that supports production. The methods and apparatus must also provide that the sensor energy enters the composite part volume very close to the local perpendicular at the inspection site.

SUMMARY

Although the embodiments disclosed in detail herein relate to methods and apparatus for automated ultrasonic inspection of a changing, poorly defined or unknown shape, it should be appreciated that the scanning mechanisms disclosed herein are equally useful in other applications that involve scanning a sensor over an unknown surface. The scanning system disclosed herein can be used to scan many different types of sensors over an unknown surface.

When used in nondestructive inspection of a fabricated component, the scanning system must be capable of inspecting at a rate that supports production. An example of a primary use of this scanning system would be for the inspection of a variable radius or a noncircular radius produced using soft tooling to form a composite structure, such as an integrally stiffened wing box of an aircraft.

One embodiment disclosed herein has a mechanical design that allows a linear ultrasonic array to adjust to the "as inspected" shape of the radius, which is not known before the inspection. The system then uses combined rotational (i.e., sweeping) and translational (i.e., traveling) motions to scan the inspection surface. This will allow an inspection to take place at a rate that supports production.

To provide a normal (i.e., perpendicular) sound entry and facilitate inspection at the required high rate, a linear ultrasonic transducer array (also referred to herein as a "sensor") is oriented lengthwise down the length of the radius and is mechanically pressed into the "as inspected" radius at 90 degrees so that sound entering the radius will enter normal to the front surface of the radius. The sensor is then swept back and forth in the radial direction so that each part of the radius is inspected. The scanning mechanism is designed to keep the sensor normal to the front surface of the radius at all times. Simultaneous with its radial sweeping motion (i.e., oscillation), the radius scanner is translated down the length of the radius during movement of the tractor. The result is that the sensor makes a simultaneous oscillating and translating motion that covers the entire radius, with the sensor always normal to the surface at a high area coverage rate.

In accordance with one embodiment, a sensor is incorporated in a toppler. (As used herein, the term "toppler" refers to a rotatable sensor-holding fixture.) The toppler is supported by a sensor position adjustment mechanism. The latter is slidable relative to nonsliding portions of the scanner mechanism in a way that mechanically presses the sensor against the radius surface so that the sensor adjusts on the fly to the as-inspected shape. The scanner mechanism is carried by a trailer vehicle that is pulled along the radius by a self-propelling tractor vehicle which is magnetically coupled to the trailer vehicle. As a result of this arrangement, the sensor can undergo a back-and-forth sweeping motion as it rotates about an axis that is generally parallel to the radius, coupled with motion along the radius. The sweeping sensor is further able to displace radially relative to a sweep pivot axis and rotate (hereinafter "topple") about a topple pivot axis. In this manner, the orientation of the sensor can adjust to the contour of the inspected surface as the sensor sweeps up and down while steadily moving along the radius at a preset speed. The unique motion of the sensor allows this inspection method to meet production rate requirements.

In accordance with one aspect, a scanning system is provided which comprises a support assembly, a scanner assembly, and a sensor. The scanner assembly comprises a pivotable subassembly pivotably coupled to the support assembly for pivoting about a sweep axis and a sensor position adjustment subassembly translatably coupled to the pivotable subassembly. The pivotable subassembly comprises first and second linear motion guide halves, while the sensor position adjustment subassembly comprises third and fourth linear motion guide halves coupled to the first and second linear motion guide halves respectively to guide the sensor position adjustment subassembly to move linearly relative to the pivotable subassembly in a direction normal or nearly normal to the sweep axis. The sensor position adjustment subassembly further comprises a sensor holder that holds the sensor and is pivotably coupled to the third and fourth linear motion guide halves.

In accordance with another aspect, a scanning system is provided which comprises: a support assembly; first and second sweep drive axles pivotably coupled to the support assembly; first and second linear guides respectively attached to the first and second sweep drive axles; first and second sliding assemblies respectively coupled to the first and second linear guides for sliding displacement therealong; a toppler pivotably coupled to the first and second sliding assemblies; and a sensor held by the toppler.

In accordance with a further aspect, a scanning system is provided which comprises: a support vehicle; a sensor; a scanner assembly that is pivotably coupled to the support vehicle for pivoting about a sweep axis, wherein the scanner assembly comprises a sensor position adjustment subassembly that can move linearly in a direction normal to the sweep axis, and the sensor position adjustment subassembly comprises first and second non-pivotable portions and a sensor holder that holds the sensor and is pivotably coupled to first and second non-pivotable portions; a first motor mounted to the support vehicle and coupled to the scanner assembly, the first motor driving pivoting of the scanner assembly when actuated; a second motor which causes the support vehicle to move when actuated; and a motor controller programmed to control the first and second motors to operate in a synchronized manner such that a velocity of the support vehicle depends on a length of the sensor and a cycle rate and sweep angle range of the scanner assembly.

Another aspect is a method for scanning a filleted join region of a hollow structure using a sensor supported on a pivotable assembly mounted on a mobile platform, comprising: (a) placing the mobile platform inside the hollow structure with the sensor proximate to the filleted join region; (b) actuating a first motor to cause the mobile platform to travel along the filleted join region; (c) controlling a second motor to cause the pivotable assembly to oscillate through a range of sweep angles; (d) controlling the sensor so that it directs radiation toward the filleted join region; and (e) urging a slidable subassembly that holds the sensor toward the filleted join region, wherein at least steps (b), (c) and (e) are performed concurrently.

Other aspects are disclosed and claimed below.

BRIEF DESCRIPTION OF THE DRAWINGS

FIG. 1 is a diagram showing an orthographic view of a portion of a generalized integrally stiffened wing box of an airplane having top and bottom skins or panels connected by a plurality of spars.

FIG. 2 is a diagram showing a side view of a tractor-trailer configuration that includes an active trailer vehicle above and a tractor vehicle below a bottom skin of an integrally stiffened wing box. (A passive trailer vehicle on the other side of the spar is not visible.) The left-hand side of FIG. 2 shows an inspection scenario wherein the trailer vehicles are inverted, while the right-hand side shows an inspection scenario wherein the tractor vehicle is inverted.

FIGS. 11 through 13 are diagrams showing side, sectional and end views respectively of a sweeper bridge assembly in accordance with one embodiment.

FIG. 14 is a diagram showing an isometric view of a toppler assembly in accordance with one embodiment.

FIG. 15 is a diagram showing an end view of a portion of the toppler assembly depicted in FIG. 14.

DETAILED DESCRIPTION

Figure 3:
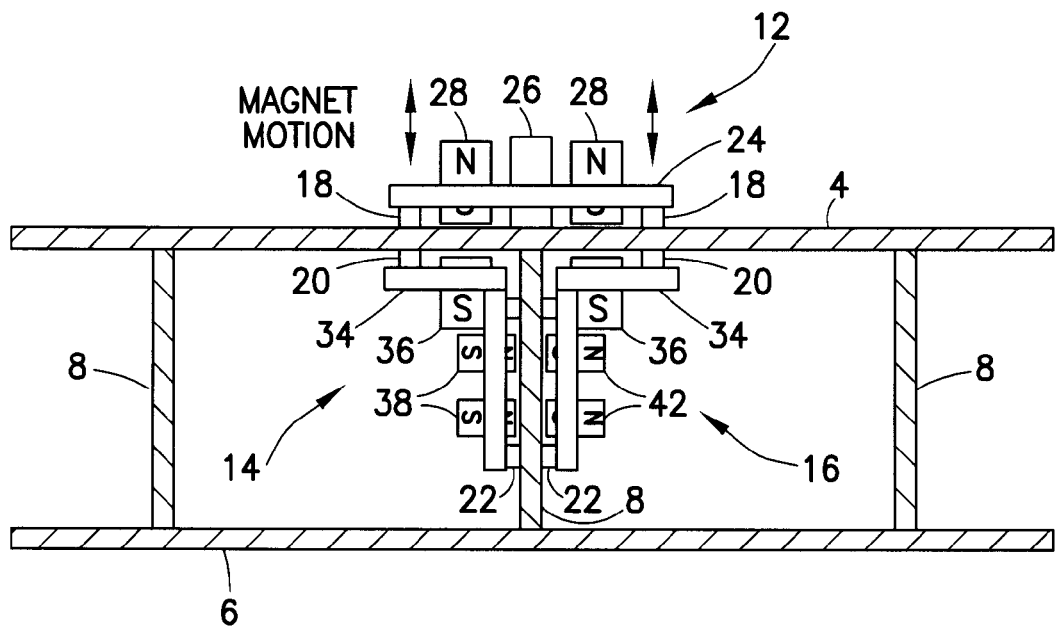
FIG. 3 is a diagram showing an end view of the tractor-trailer configuration depicted on the left-hand side of FIG. 2 (with respective inverted trailer vehicles disposed on both sides of a spar).

In accordance with one embodiment, ultrasonic NDI sensors are used to inspect a hollow monolithic composite structure, such as an integrally stiffened wing box for an aircraft (e.g., a horizontal stabilizer). A portion of a generalized integrally stiffened wing box 2 is depicted in FIG. 1. The depicted integrally stiffened wing box comprises a top skin 4 and a bottom skin 6 connected by a plurality of a plurality of internal vertical support elements, hereinafter referred to as "spars". Each spar comprises a web 8 and respective pairs of filleted join regions 10 (also called "spar radii" herein), which connect the spar web 8 to the top and bottom skins. As used herein, the terms "top skin" and "bottom skin" refer to the relative positions of two skins of a wing box during inspection, not when the wing box is installed on an airplane (i.e., a wing box may be inverted for inspection).

Inspecting large soft-tooled monolithic composite structures to ensure structural integrity presents four distinct yet interrelated challenges. (1) The interior of the part is often inaccessible to conventional ultrasonic scanning systems. (2) The entire interior surface of the structure may need to be inspected. (3) The production manufacturing of composite structure for an active airplane program must be done at a rate that meets schedule commitments. (4) Soft-tooled composites have surfaces, particularly spar radii, which are not precisely defined.

In accordance with one embodiment, an ultrasonic linear array (i.e., sensor) is transported down the length of a tunnel through the interior of the composite structure. For this type of inspection, the sensor is carried by a trailer vehicle (not shown in FIG. 1) placed inside the hollow structure 2. This trailer vehicle can be characterized as being "active" in the sense that equipment it carries is actively performing a scanning function. The sensor needs to be acoustically coupled to each surface being inspected while an automated tractor vehicle (also not shown in FIG. 1) moves the trailer vehicle along that surface in a region of interest. This is accomplished by providing a column of water that flows between the sensor and the inspected part.

In FIG. 1, portions of the interior surfaces of the part which need to be inspected can be seen. Each spar may need to have all four filleted join regions 10 and each web 8 inspected. This is a challenging inspection as each cavity is essentially a long rectangular tunnel that may increase or decrease in cross section as one moves from one end to the other. The top and bottom skins 4 and 6 can be inspected from the exterior using conventional NDI techniques which are not part of this disclosure In accordance with one embodiment for inspecting structures of the type shown in FIG. 1, an external motorized and computer-controlled tractor is magnetically coupled to an internal active trailer that holds and positions one or more ultrasonic transducer arrays on the interior of the part. Also, there is an internal passive trailer on the opposite side of the spar that is magnetically coupled through the spar to the active trailer and also magnetically coupled through the skin to the tractor. This three-part system gives a very stable system for positioning and moving the ultrasonic transducers. One embodiment of such a three-part system will now be described with reference to FIGS. 2 and 3.

FIG. 2 shows side views of a tractor-trailer configuration in accordance with one embodiment in two different inspection situations (motor actuators are not shown). The automated NDI inspection system comprises a traction-motor powered tractor vehicle 12, which rides on the external surface of top skin 4 or bottom skin 6 of integrally stiffened wing box 2, and a pair of trailer vehicles (only trailer vehicle 14 is visible in FIG. 2, the other being hidden behind a spar web 8), which ride along an internal surface of the top or bottom skin. The left-hand side of FIG. 2 shows an inspection scenario wherein the tractor vehicle 12 is outside the integrally stiffened wing box in a non-inverted position while the trailer vehicles are inside the integrally stiffened wing box in inverted positions; the right-hand side of FIG. 2 shows an inspection scenario wherein the tractor vehicle 12 is outside the integrally stiffened wing box in an inverted position while the trailer vehicles are inside the integrally stiffened wing box in non-inverted positions. FIG. 3 shows an end view of the tractor-trailer configuration depicted on the left-hand side of FIG. 2, with inverted trailer vehicles 14 and 16 disposed on opposite sides of the spar web.

In the inspection scenario depicted in FIG. 3 (and the left-hand side of FIG. 2), idler wheels 18 of tractor vehicle 12 contact and roll on the external surface of top skin 4 while vertical idler wheels 20 of inverted trailer vehicles 14 and 16 (only one such idler wheel is visible in FIG. 3 for each trailer vehicle) contact and roll on the internal surface of top skin 4, and the horizontal idler wheels 22 roll on the spar web surface. The right-hand side of FIG. 2 show an alternative situation wherein idler wheels 18 of the inverted tractor vehicle 12 contact and roll on the external surface of bottom skin 6 while vertical idler wheels 20 of trailer vehicle 14 (and also idler wheels of trailer vehicle 16 not visible in FIG. 2) contact and roll on the internal surface of bottom skin 6, and the horizontal idler wheels 22 roll on the spar web surface.

In accordance with the embodiment partly depicted in FIGS. 2 and 3, the tractor vehicle 12 comprises a frame 24. Four idler wheels 18 (only two of which are visible in each of FIGS. 2 and 3) are rotatably mounted to frame 24 in a conventional manner. (Alternative embodiments may include more idler wheels.) The idler wheels 18 are made of plastic and have smooth contact surfaces. Tractor vehicle motion is enabled by driving a drive wheel 26 (also rotatably mounted to frame 24) to rotate. Drive wheel 26 is coupled to a motor 30 via a transmission (not shown). The drive wheel 26 is positioned on the frame 24 so that it is in frictional contact with skin 4 or 6 when idler wheels 18 are in contact with the same skin. The drive wheel is made of synthetic rubber material. The surface of the drive wheel may have a tread pattern. In addition, the tractor vehicle 12 carries multiple permanent magnets 28. Each permanent magnet 28 has North and South poles, respectively indicated by letters "N" and "S" in the drawings.

Still referring to FIGS. 2 and 3, each trailer vehicle 14, 16 is comprised of a frame 34. For each trailer vehicle, two vertical idler wheels 20 (only one of which is visible in FIG. 3) and four horizontal idler wheels 22 (only two of which are visible in FIG. 3) are rotatably mounted to frame 34 in a conventional manner. (Alternative embodiments may include more idler wheels.) Each trailer vehicle 14, 16 carries multiple vertically mounted permanent magnets 36, the North poles of which are magnetically coupled to the South poles of confronting permanent magnets 28 carried by the tractor vehicle 12. In the design described by FIGS. 2 and 3, each trailer has two vertically mounted permanent magnets 36, but other designs may use different configurations. The positions and pole orientations of the magnets may have other configurations as long as the N-S pairing and relative alignment of the magnets between the tractor and trailer are preserved.

As seen in FIG. 3, in addition to being magnetically coupled to the tractor vehicle 12, the trailer vehicles 14 and 16 are magnetically coupled to each other using additional sets of permanent magnets 38 and 42. As seen in FIG. 2, trailer vehicle 14 carries four horizontally mounted permanent magnets 38. Trailer vehicle 16 also carries four horizontally mounted permanent magnets 42 (only two of which are visible in FIG. 3), the poles of which are respectively magnetically coupled to opposing poles of the permanent magnets 38 on trailer vehicle 14. This magnetic coupling produces an attraction force that holds idler wheels 22 of trailer vehicles 14 and 16 in contact with opposing surfaces of an intervening spar.

As seen in FIG. 2, trailer vehicle 14 further carries a payload 40. For the NDI scenario depicted in FIGS. 2 and 3, payload 40 is an oscillating motion mechanism attached to an ultrasonic NDI sensor which is acoustically coupled to the internal surface being inspected. For example, the inspected region may be sprayed with water to acoustically couple the ultrasonic sensor to a spar web 8 or a filleted join region 10. Magnetically coupled systems are well suited for operation with water in the environment. The orientation and scanning movement of payload 40 will depend on which portion of the wing box internal surface is to be inspected.

As the tractor vehicle is driven to travel along a desired path on the outer surface of the top or bottom skin, it pulls the inner trailer vehicles along. The magnetic coupling system described above keeps the inverted vehicle(s) in contact with the surface it rides on. For wing box applications, two magnetically coupled trailer vehicles can be used, one on each side of the spar, as shown in FIG. 3. This allows the system to take advantage of the internal structure of the scanned object as a guide to allow the system to track properly along the surface.

The system partly depicted in FIGS. 2 and 3 further comprises means (not shown) for automatically adapting to the variable thickness of the intervening skin or panel (i.e., top skin 4 or bottom skin 6) by raising or lowering the magnets (which magnet motion is indicated by double-headed arrows in FIG. 2) on the tractor vehicle as it moves along the structure being inspected. Further details concerning the trailer-tractor configuration depicted in FIGS. 2 and 3 and other embodiments are disclosed in U.S. patent application Ser. No. 13/313,267, the disclosure of which is incorporated by reference herein in its entirety.

The basic concept of the tractor/trailer transport system described above can be adapted as necessary to perform different scanning operations, such as scanning the edge and central portions of each web 8 and the four filleted join regions 10 that join each web to the top and bottom skins (two at the top skin 4 and two at the bottom skin 6). While it is advantageous to use the same tractor for each of the different scanning operations that make up the overall inspection process, a different active trailer can be used to perform each respective specific scanning operation.

This in turn may require the use of a respective passive trailer specifically adapted to magnetically couple with a respective active trailer. This disclosure will describe methods and apparatus for inspecting filleted join regions 10 (hereinafter "radii") of an elongated and tapered hollow structure. The active trailer for scanning a spar radius will be referred to herein as a "spar radius scanner". In the embodiment shown in FIG. 3, the trailer vehicle 14 is designed to work with the tractor on the top or bottom of the integrally stiffened wing box (or other composite structure having cavities between webs). The trailer vehicle 14 comprises apparatus which holds and positions a sensor. The sensor simultaneously sweeps and translates as it moves down the length of a "radius" formed by a surface of a filleted join region 10. The trailer vehicle 14 (hereinafter "radius scanner") is designed to adjust the position and orientation of the sensor so that its beam stays normal (or nearly normal) to a soft-tooled radius that varies in shape. The radius scanner may also have a video camera (not shown) that captures a live view of the scan head.

The radius scanner uses a sensor in a way that provides a normal (perpendicular) sound entry and facilitates inspection at a sufficiently fast rate. In the case of a linear ultrasonic array, the array is oriented lengthwise down the length of the spar radius and is held in firm contact with the "as inspected" radius at 90 degrees so that sound entering the spar radius will enter normal to the front surface of the spar radius. The array is then swept back and forth in the tangential direction so that each part of the radius is inspected as the tractor/trailer system travels along the radius. The scanning mechanism is designed to keep the sensor normal to the front surface of the spar radius at all times. Simultaneous with the sweeping motion of the sensor, the radius scanner is translated down the length of the radius during movement of the tractor vehicle. The result is that the ultrasonic linear array, which is generally aligned with the radius, makes a simultaneous oscillating and translating motion that covers the entire spar radius with ultrasonic beams that are always normal (or nearly normal) to the surface at a high area coverage rate.

The motion control for the radius scanning system comprises three parts: the X-axis position control, the angular position control, and a synchronization process.

The X-axis motion (the X axis being parallel to the spar radius being inspected if the spar radius is linear) is provided by the tractor vehicle of the system, which uses data from a rotational encoder attached to an idler wheel on the trailer vehicle. The trailer component is pulled by the tractor and carries the scanner assembly. The X-motion drive motor and the sweeping motion drive motor are programmable stepper motors that can communicate with a personal computer through a serial communications interface. The operator or automated path planning system specifies the desired steady-state speed, direction, and an optional final goal position of the tractor-trailer system through a motion control software application. The X-axis positioning is controlled using proportional feedback of the encoder count data. Other types of servo motors with encoders can be used in place of stepper motors.

The process for controlling the sweeping motion (i.e., angular position) of the scanner assembly takes advantage of an on-board microprocessor in a stepper motor unit. A cyclic motion form is programmed into the motor, which takes cycle time, motion extents, and maximum acceleration data as the inputs. The system also uses a limit switch for calibrating the home angular position of the system.

When the X-direction motion of the tractor and the cyclic sweeping motion of the scanner assembly are used together, the resulting motion is a sawtooth path with rounded peaks and valleys (due to acceleration/deceleration). When operated at the appropriate speed, a continuous area scan will be created.

If the X-direction motion of the tractor is too fast, gaps will appear in the scan data. To address this issue a process has been developed to synchronize the X-direction velocity of the tractor with the motion of the oscillating sensor mechanism. This process uses the cycle rate, angular motion range, and sensor width to compute the appropriate tractor velocity. The process also has a scaling variable to ensure that there is a small amount of overlap to compensate for minor fluctuations in velocity as the system moves (such as velocity disturbances transmitted by the tractor-trailer coupling system).

Once the fixed parameters of sensor width, angular motion range and overlap are set, the entire process can be controlled by a single variable—the cycle rate. This will compute and set the X-direction velocity of the tractor to provide full scan area coverage without gaps in the data.

Figure 4A:
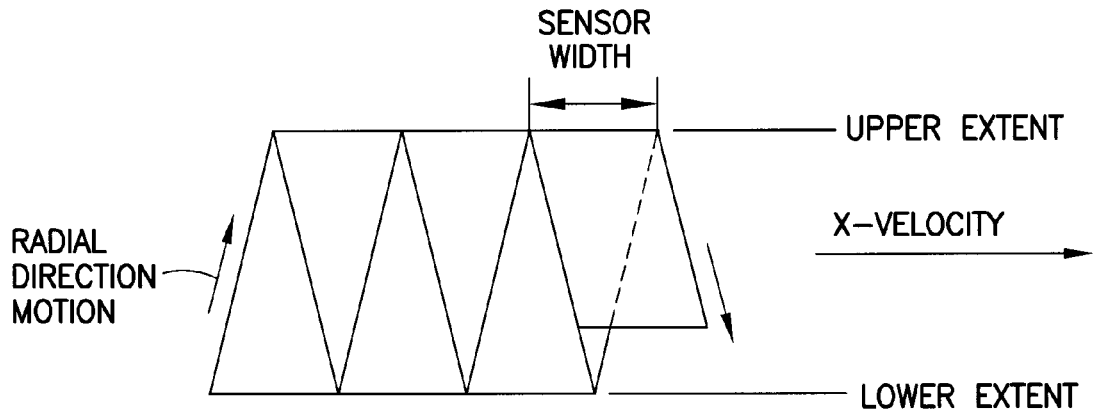
FIGS. 4A through 4C are diagrams showing different radius scan patterns: (A) exact coverage pattern; (B) X velocity too large (or cycle rate too slow); and (C) pattern with a small amount of overlap.
Figure 4B:
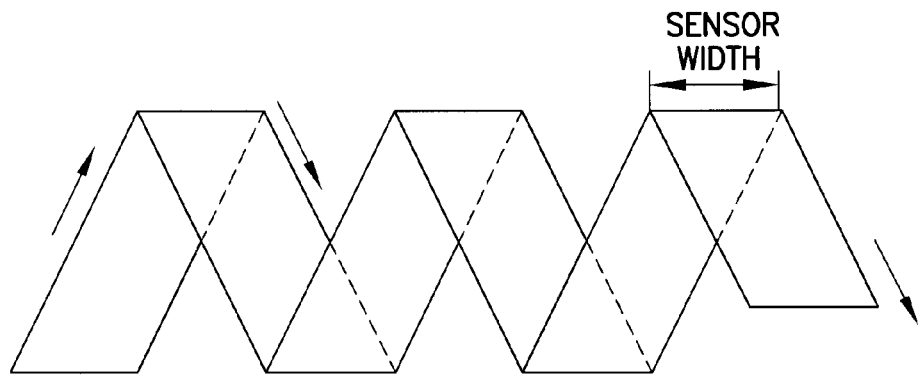
Figure 4C:
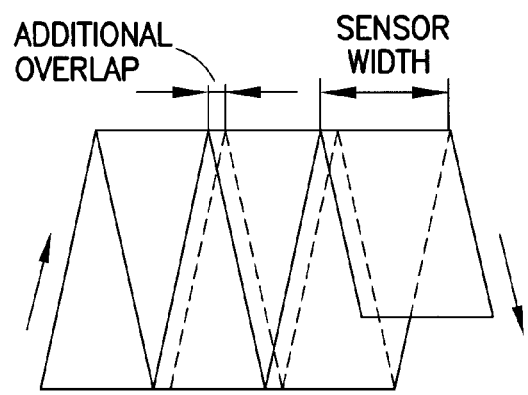

FIGS. 4A through 4C illustrate the different aspects of this motion synchronization, showing three potential coverage patterns. FIG. 4A shows the exact coverage pattern with no overlap and no gaps, but this pattern could produce gaps if the X-direction speed were to fluctuate. FIG. 4B shows the pattern when the X-velocity is too high, or equivalently if the cycle rate is too slow. FIG. 4C shows the pattern with a small amount of overlap. The overlap ensures coverage when the X-direction speed fluctuates by less than a specified amount, the amount of overlap needed being a function of the maximum fluctuation to be expected.

Figure 5:
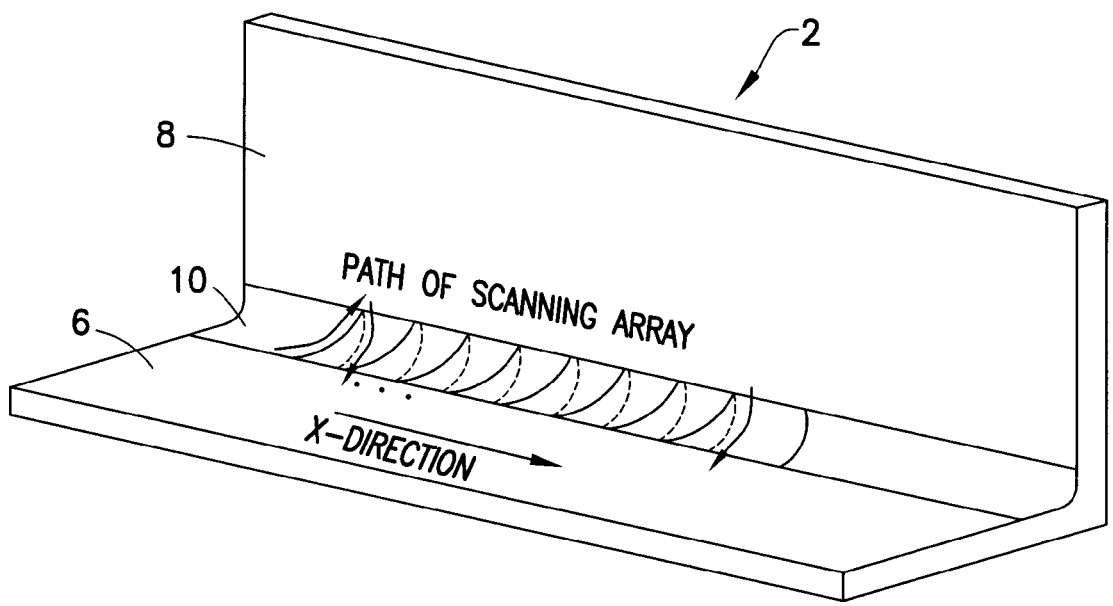
FIG. 5 is a diagram showing an isometric view of a portion of an integrally stiffened wing box with a radius scan pattern imposed thereon. The solid and dashed curved lines respectively represent alternating upward and downward scans as the scanner travels along the length of the radius.

FIG. 5 is a diagram showing an isometric view of a portion of an integrally stiffened wing box with a radius scan pattern (of the type shown in FIG. 4A) imposed thereon. The solid and dashed curved lines respectively represent alternating upward and downward scans as the radius scanner travels at a constant speed along the length of the spar radius (i.e., in the X-direction).

Besides the unique motion of the ultrasonic array, an important part of solving the problem of a non-uniform "radius" is ensuring that the sound enters the part at or nearly at 90 degrees or normal to the front surface. It is important to keep the direction of ultrasound entry normal to the radius front surface during the entire sweep of the spar radius. If the spar radius were truly circular, that would less challenging.

The spar radius that results from soft-tooled composites parts, whether they are designed to be constant or to vary by part location, will "vary by manufacturing". This fact creates a difficult and unique mechanical challenge to design and build an apparatus that can maintain sensor-to-part surface normality over the entire sweep of the radial motion and over a challenging and not-known-in-advance variety of "radial" shapes. In accordance with one embodiment, the ability to maintain normality over an unknown "radius" is provided using the mechanical design described hereinafter.

Figure 6:
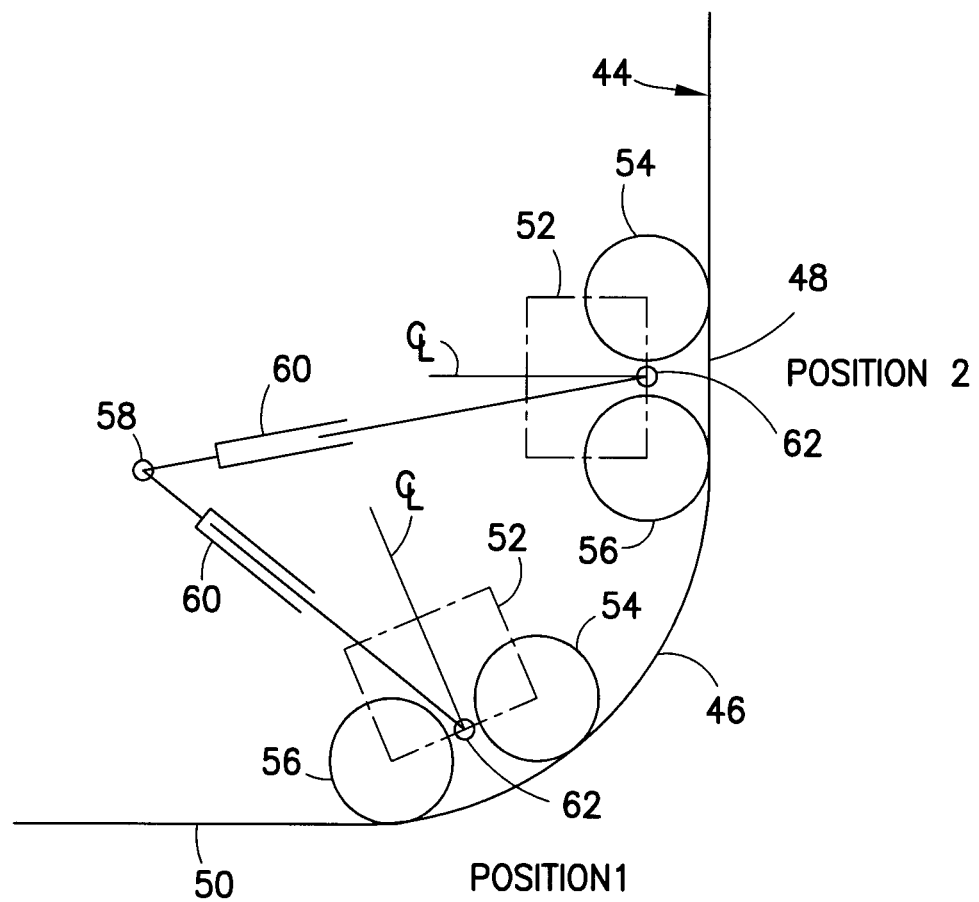
FIG. 6 is a schematic representation of a combined sweeping and toppling motion of a sensor in accordance with one embodiment.

FIG. 6 illustrates a cross section of the surface 44 of a part comprising a circular fillet 46 between two flanges 48 and 50. A fixture 52 (referred to hereinafter as a "toppler") holds the sensor (not shown) perpendicular to a centerline CL between two surface followers 54 and 56. These followers 54, 56 may be rolling wheels of various shapes, or solid rubbing blocks, depending upon the requirements of the particular part being inspected and the required duration of the inspection. Note that as this sort of assembly is swept along the surface, the centerline CL through the sensor remains normal to the local surface 44 between the followers 54, 56. It should be noted that the spacing between the two followers should be selected according to the expected degree of surface variability. In other words, a surface whose curvature changes rapidly needs followers that are closer together.

Some means for sweeping around the inspected range of travel must be provided, and one method is illustrated in FIG. 6. A fixed position pivot 58, called the "sweep pivot", is held at some location in space relative to the part surface 44, by means of one of any number of different types of carriage mechanisms (such mechanisms are well known). A telescoping pressure slide 60, swept through a range of angles, is used to push the toppler 52 against the surface 44 of the part, by means of a topple pivot 62 placed as near to the surface 44 as possible so as to minimize the tendency of the toppler 52 to "topple" if it encounters an obstruction during the sweep. The slide 60 may telescope toward the surface 44 due to forces exerted by springs, hydraulic or pneumatic actuators, or other means for applying force along a direction. Pivot 58 is driven by a motor (not shown) in an oscillating pattern to produce sweep coverage of the fillet 46, plus a small amount of the flat surfaces 48 and 50 near fillet 46.

In accordance with one embodiment, the scanning system comprising a support assembly, a sweeper bridge assembly pivotably coupled to the support assembly for pivoting about a sweep axis (i.e., the axis of sweep pivot 58 in FIG. 6), and a sensor carried by the sweeper bridge assembly. The sweeper bridge assembly in turn comprises a sensor position adjustment subassembly (comprising toppler 52 in FIG. 6) that allows the sensor to move in a direction normal or nearly normal to the sweep axis and orient so that its centerline is normal or nearly normal to the surface being inspected. The adjustment of the sensor orientation is enabled by the toppler, which is pivotable about a topple axis (i.e., the axis of topple pivot 62 in FIG. 6).

Figure 7A:
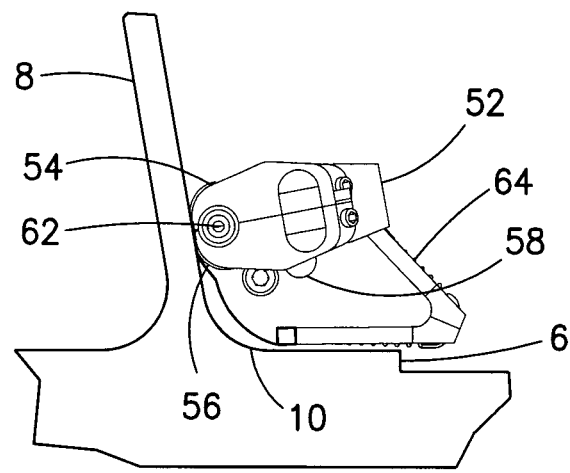
FIGS. 7A through 7F are diagrams showing respective relative positions of a toppler and a sweep bridge during sweeping.
Figure 7B:
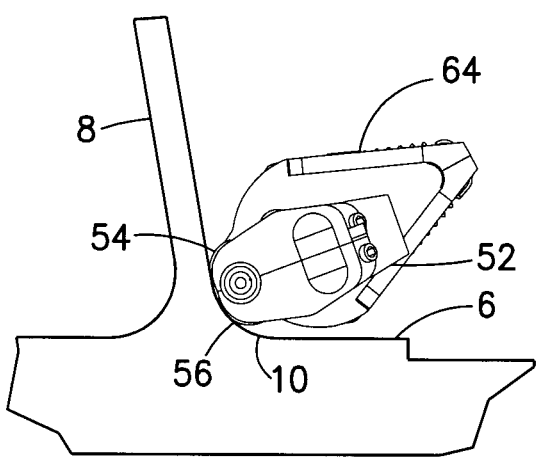
Figure 7C:
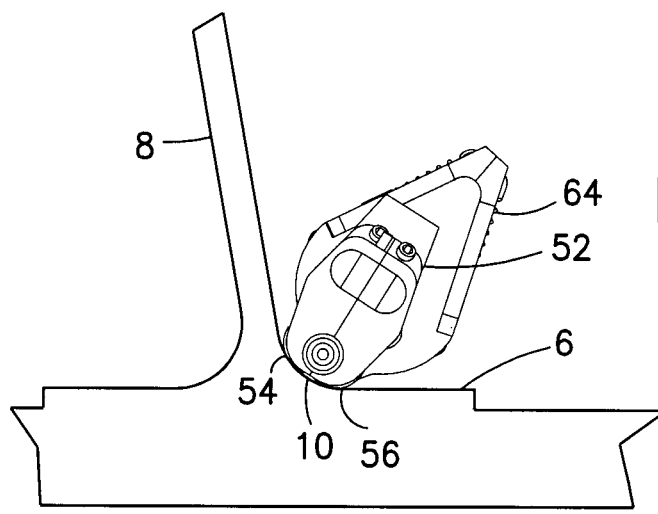
Figure 7D:
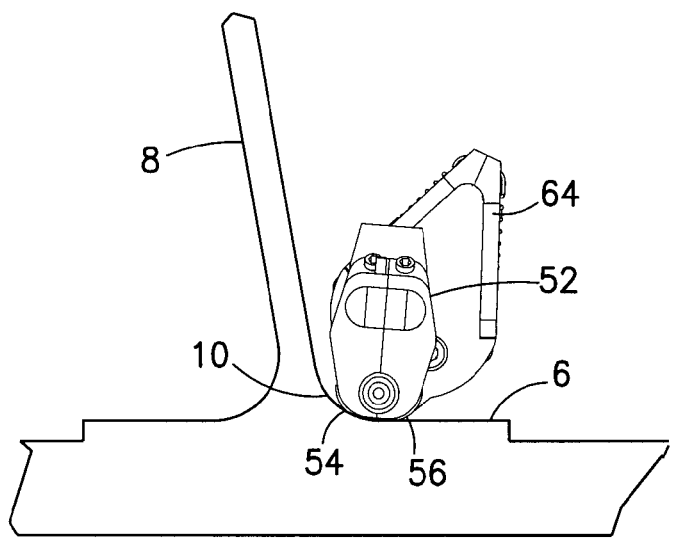
Figure 7E:
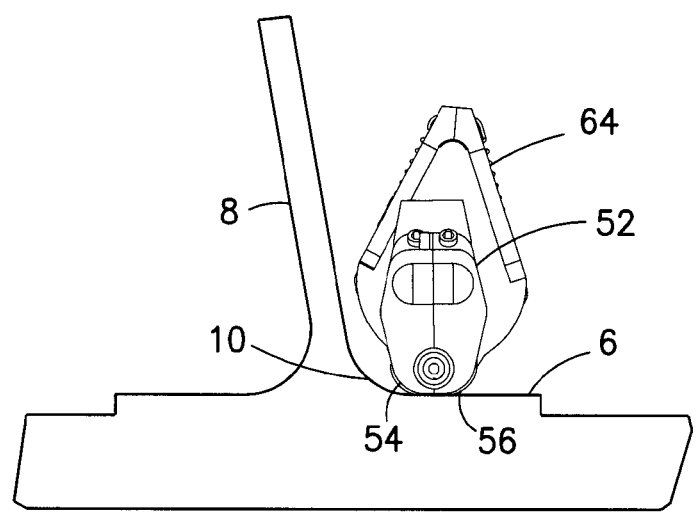
Figure 7F:
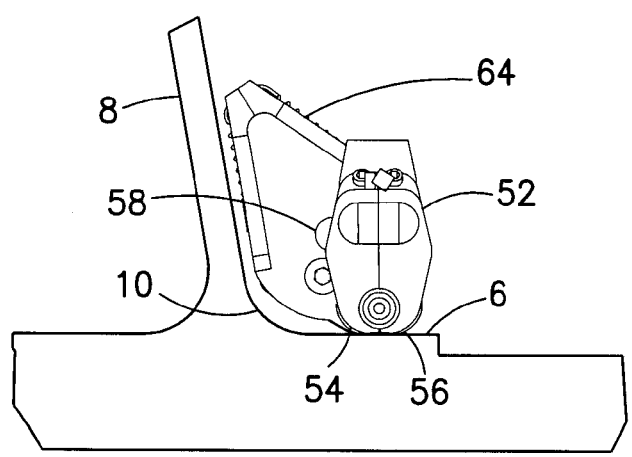

Relative positions of the toppler 52 and a bridge assembly 64 (in this embodiment, both are components of the sensor position adjustment subassembly) during scanning of a surface of a part are shown in FIGS. 7A through 7F. In this example, the part comprises a flange or bottom skin 6 having a flat surface, a spar web 8 having a flat surface, and a fillet 10 having a non-circular "radius". The toppler 52 comprises two pairs of surface follower wheels 54, 56, only one pair of which is visible in FIGS. 7A-7F. In FIG. 7A, both wheels 54, 56 are on the flat surface of web 8 and the sweep angle of the bridge assembly is at a maximum in one direction; in FIG. 7B, wheel 54 is on the flat surface of web 8 while wheel 56 is on the "radius" of fillet 10; in FIG. 7C, both wheels 54, 56 are on the "radius" of fillet 10; in FIG. 7D, wheel 54 is on the "radius" of fillet 10 and wheel 56 is on the flat surface of bottom skin 8; in FIG. 7E, both wheels 54, 56 are on the flat surface of bottom skin 8; and in FIG. 7F, both wheels 54, 56 are on the flat surface of bottom skin 8 and the sweep angle of the bridge assembly is at a maximum in an opposite direction.

As seen in FIGS. 7A-7F, the scanning mechanism is designed to keep the sensor normal to the front surface of the radius at all times. Simultaneous with its radial sweeping motion (i.e., oscillation), the scanning mechanism is translated down the length of the radius by movement of a support vehicle. The result is that the sensor makes a simultaneous oscillating and translating motion that covers the entire radius, with the sensor always normal to the surface at a high area coverage rate.

Figure 8:
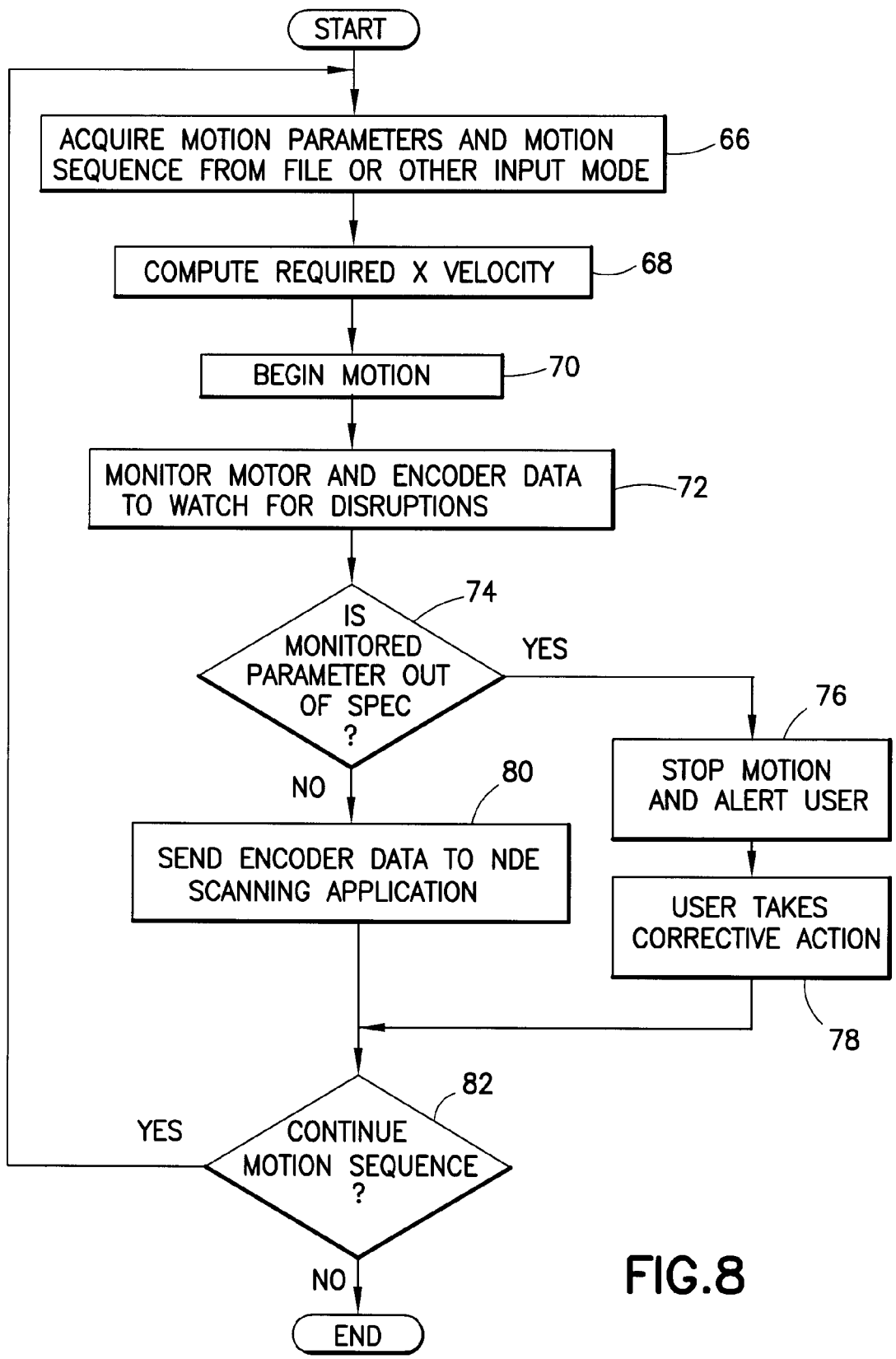
FIG. 8 is a flow chart showing a motion control algorithm in accordance with one embodiment.

FIG. 8 is a flowchart showing steps of a process for controlling the motion of the radius scanner and the rotation of the scanner assembly onboard the radius scanner. First, the motion parameters and a motion sequence are acquired from or file or other input mode (step 66). Then the required speed of the radius scanner in the X-direction is computed (step 68). The coordinated motion of the radius scanner and rotation of the scanner assembly are started (step 70). During these coordinated movements, motor and encoder data are monitored to watch for disruptions (step 72). The motion controller (e.g., a personal computer connected to the apparatus by means of electrical cables) continuously determines whether any monitored parameter has a value outside of a specified range (step 74). If a parameter value is outside its specified range, the motion of the radius scanner and rotation of the scanning assembly are stopped and the system operator is alerted (step 76). The system operator then takes corrective action (step 78). After corrective action has been taken, a determination is made whether to continue the motion sequence (step 82). If the motion sequence should be continued, the process returns to step 66; if it should not continue, then the process is not resumed. If step 74 determines that no parameter values are outside their specified ranges, then encoder data is sent to the NDI scanning application running on the motion controller (step 80). Then step 82 is repeated. When the encoder data indicates that the radius scanner has reached a termination point during its travel in the X-direction, the motion sequence will be discontinued.

One implementation of a radius scanner equipped with a scanning system of the type described above will be hereinafter described with reference to FIGS. 9-16. In particular, the operation of this system will be described with reference to a web/flange joint (not shown in FIGS. 9-16, but see web 8 and flange 4 in FIG. 3).

Figure 9:
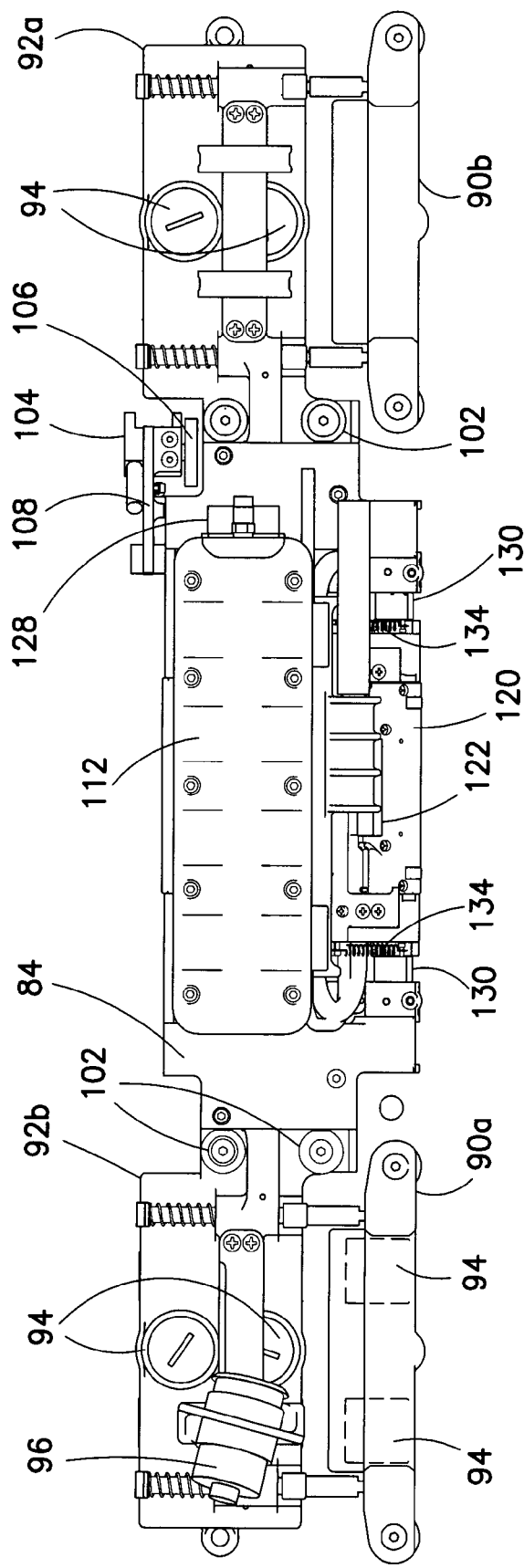
FIGS. 9 and 10 are diagrams showing top and side views of a trailer vehicle that carries the radial sweeping mechanism, toppler and sensor disclosed herein during nondestructive inspection of a radius.
Figure 10:
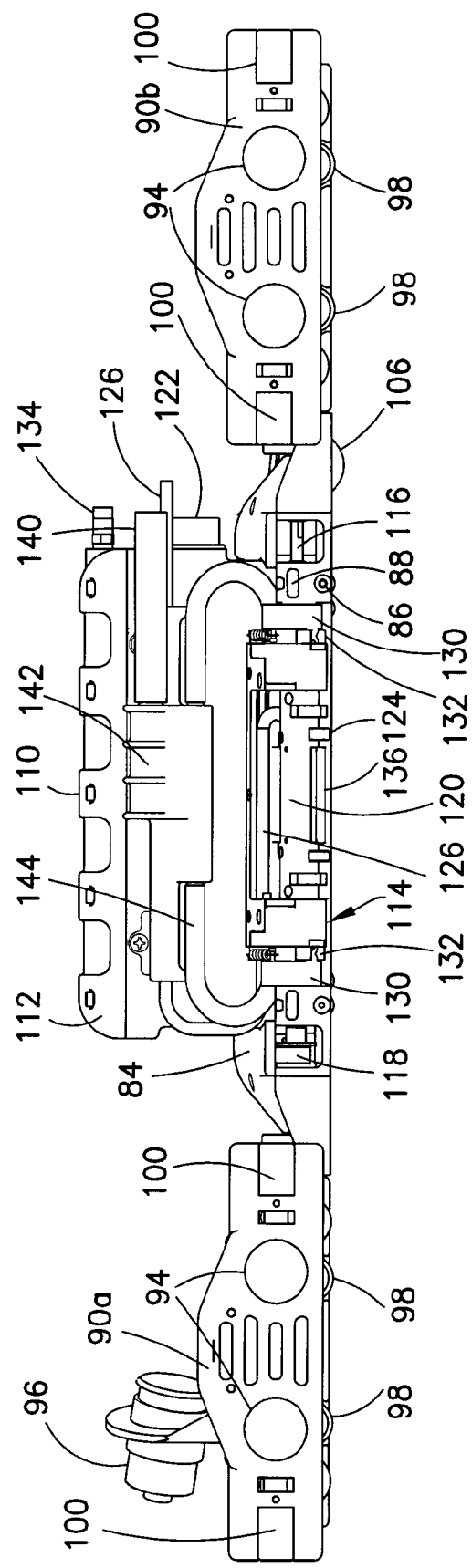

FIGS. 9 and 10 respectively show top and side views of a radius scanner in accordance with one embodiment. The radius scanner comprises a probe body 84. The probe body 84 has four web probe body wheels 86 that bear against a web and two flange probe body wheels 88 that bear against a flange. The probe body rolls on wheels 86 and 88 as it follows the spar radius being inspected.

The radius scanner is magnetically coupled to a tractor vehicle on the other side of a flange by means of two flange magnet trolleys 90a, 90b and to a second trailer vehicle on the other side of a web by means of two web magnet trolleys 92a, 92b. Each magnet trolley carries a pair of magnets 94 for magnetic coupling to magnets of opposite polarity carried by the tractor vehicle and other trailer vehicle, as previously described. A monitoring camera 96 is mounted on one web magnet trolley 92b (see FIG. 9). Each web magnet trolley has four wheels 98 (only two are visible in FIG. 10), which roll over the web surface. Each flange magnet trolley has two wheels 100, which roll over the flange surface.

As best seen in FIG. 9, each flange magnet trolley 90a, 90b is adjustably mounted to a corresponding web magnet trolley 92a, 92b. The latter, in turn, are respectively coupled to opposite ends of the probe body 84. Each coupling includes a pair of spring-loaded probe pressure axes 102, which press the probe body 84 against the web while vehicles are magnetically coupled.

Referring to FIG. 9, the X-position of the probe body 84 is measured by an X-direction encoder 104, which encodes rotation of an encoder wheel 106 mounted on the end of an encoder swing arm 108. The encoder swing arm 108 is pivotably coupled to a pin projecting from the probe body 84. The encoder wheel 106 rides on the web surface as the radius scanner travels along the spar radius. The encoder wheel 106 is shown in FIG. 10 in its extended position, which occurs when the radius scanner is lifted off of the web surface.

Referring to FIG. 10, a pivot drive module 110 is mounted on the probe body 84. An electrical connector 128 is mounted to the outside of the pivot drive module 110. The pivot drive module 110 houses a stepper motor (not shown) that drives a sweeper bridge assembly 114 to oscillate about a pair of sweeper drive axles 116. One sweep drive axle 116 is visible in FIG. 10 because a timing belt pulley has been removed for clarity. The other sweep drive axle is hidden behind the other timing belt pulley 118. The sweep drive axles are driven by the stepper motor inside the drive module 110 via respective timing belts (not shown) which circulate on the timing belt pulleys and other pulleys not visible in FIG. 10. The sweeper bridge assembly 114 comprises a pair of sweep drive flanges 130 which are respectively affixed to the sweep drive axles. The sweeper bridge assembly further comprises a sensor position adjustment subassembly (to be described in detail later with reference to FIGS. 11-13) that is translatable along a line that is normal or nearly normal to a sweep pivot axis (i.e., the common axis of the sweep drive axles) by means of respective slides 132. The sensor position adjustment subassembly is urged to translate toward the part under inspection by two pairs of springs 134 (only one spring of each pair is visible in FIG. 9).

Still referring to FIG. 9, the sweeper bridge assembly 114 supports a toppler 120 which carries a linear ultrasonic transducer array 122. As seen in FIG. 10, the toppler comprises four surface follower wheels 124, which will roll and slide sideways on the inspected surface during scanning of the type depicted in FIG. 4C. The ultrasonic transducer array 122 is connected to an ultrasonic pulser/receiver (not shown) by means of an ultrasonic array cable 126.

Ultrasonic inspection requires the presence of an acoustic couplant between the ultrasonic transducer array and the inspected part. The scanning systems disclosed herein use water as the acoustic couplant. As seen in FIG. 10, the toppler 120 has a water cavity 136 which is supplied with water via a water input tube 140, a water manifold 142 (which doubles as a handle), and a water supply tube 144 which is in fluid communication with a pair of water jet nozzles (not shown in FIG. 10; see items 162 in FIG. 12). The water jet nozzles of the sweeper bridge assembly direct water jet sprays into respective water inlets 172 disposed at opposite ends of the toppler (see FIG. 14). The water inlets 172 are in turn in fluid communication with the toppler water cavity via respective water chutes (not shown in FIG. 10, but see items 168 in FIG. 16). The pivot drive module 110 comprises a removable drive cover 112 having an air inlet 120 that supplies pressurized air to keep water out of the drive module.

FIGS. 11 through 13 show sweeper bridge assembly 114 in more detail. Referring to FIG. 11, the sweeper bridge assembly 114 comprises a sensor position adjustment subassembly that is translatable in a direction normal to the common axis (hereinafter "sweep pivot axis") of the sweep drive axles 116. Each sweep drive flange 130 is attached to the end of a respective sweep drive axle 116 and incorporates a respective male slide half. The sensor position adjustment subassembly comprises respective female slide halves 146 that are respectively slidably coupled to the male slide halves of the flange drive flanges 130.

The sensor position adjustment subassembly further comprises a pair of bridge towers 148 which are connected by a bridge 150. The female slide halves 146 are respectively attached to the bridge towers 148, which allows the subassembly (comprising female slide halves 146, bridge towers 148, and bridge 150) to translate in a direction normal or nearly normal to the sweep pivot axis. The sensor position adjustment subassembly is urged to translate toward the inspected part by two pairs of springs 134. One spring of each pair is visible in FIG. 11; two springs of one pair are visible in FIG. 13. In the view seen in FIG. 11, the springs urge the sensor position adjustment subassembly downward. The ends of each spring are respectively coupled to a spring post 152 attached to the bridge 150 and a spring post 154 attached to a sweep drive flange 130.

Each bridge tower 148 comprises a respective toppler pivot axle 156, which are inserted into respective topple pivot bearings (see item 170 in FIG. 14) installed at opposing ends of the toppler. In this manner the toppler can be pivotably coupled to the bridge towers for toppling about the common axis (hereinafter "topple pivot axis") of the toppler pivot axles 156. The bridge 150 has respective stops 158 for the flangeward and webward topple limit pins (see items 202 and 204 in FIG. 14). This arrangement limits the rotation of the toppler relative to the sensor position adjustment subassembly in both directions.

FIG. 12 is a sectional view of the sweeper bridge assembly 114, showing water inlet tubes 160 and water jet nozzles 162, by means of which water is supplied to the water chamber inside the toppler. FIG. 12 also shows a passageway 164 for the ultrasonic array cable. A water inlet tube 160 and a cable passageway 134 are visible in the end view of FIG. 13.

Figure 16:
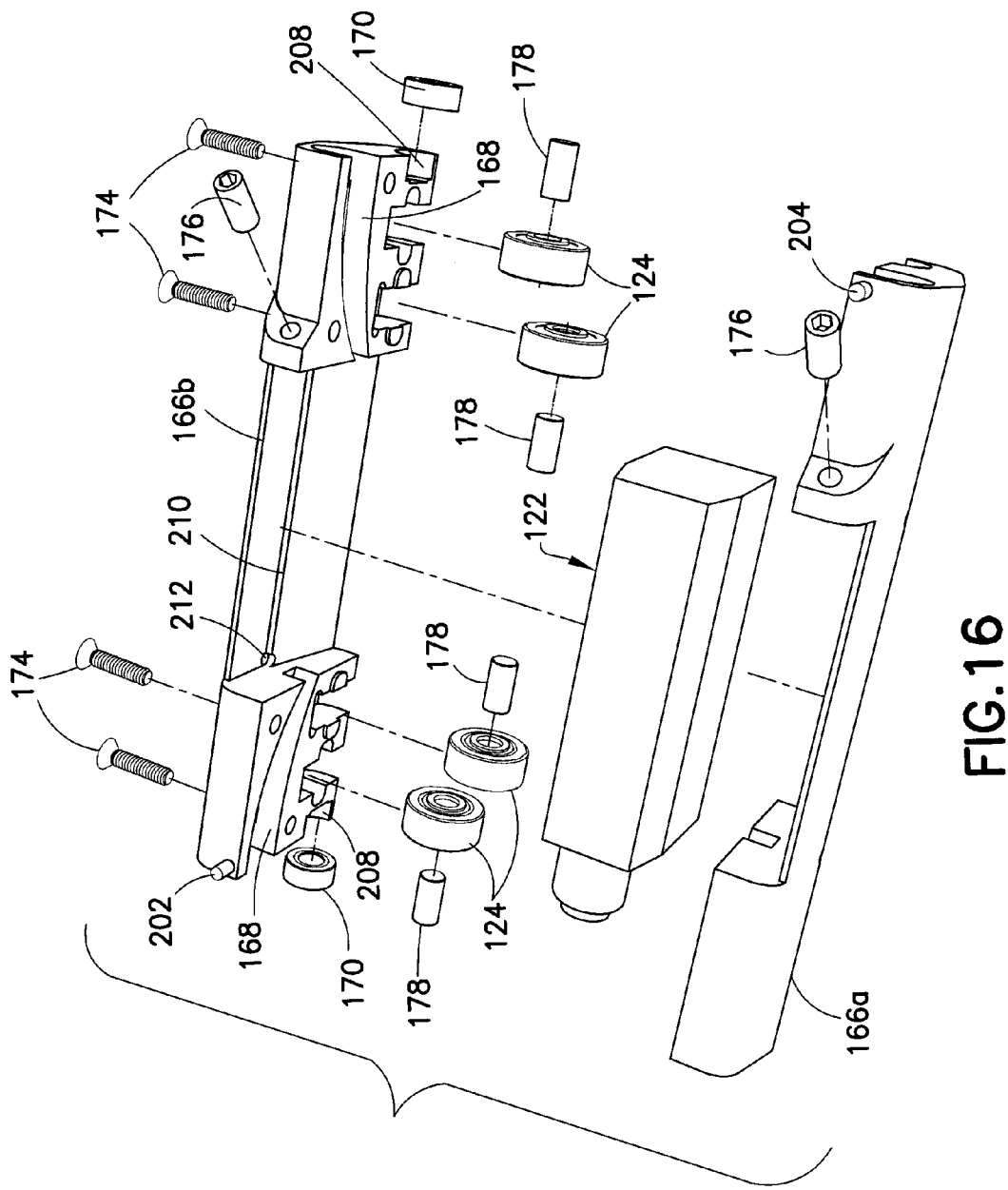
FIG. 16 is a diagram showing an exploded view of the toppler assembly and sensor.

FIGS. 14 and 16 are isometric and exploded views respectively of a toppler assembly 120 in accordance with one embodiment. Referring to FIG. 14, the ultrasonic transducer array 122 is placed inside and protrudes from the top of a toppler housing comprising web side and flange side clamshells 166a and 166b. The clamshells are fastened together using four clamshell assembly screws 174 (see FIG. 16) and are in contact at clamshell joint 206 (see FIG. 14). A plurality of water vent holes 212 (see FIG. 14) are provided in the toppler housing, for example, one at each corner of the ultrasonic transducer array face.

The protruding portion of array 122 is connected to the ultrasonic array cable 126. The active surface of the ultrasonic transducer array is opposite the exposed face seen in FIG. 14. Each clamshell has an array mounting ledge 210 (see FIG. 16). The active face of the ultrasonic transducer array is held against the surfaces of these ledges by a pair of ultrasonic array holding set screws 176, to maintain precise geometry and alignment.

FIG. 15 shows an end view of a portion of the toppler assembly depicted in FIG. 14. The outer circle 208 represents a topple pivot bearing mounting hole 208 formed in each end of the clamshell housing. A respective topple pivot bearing 170 is installed in each topple pivot bearing mounting hole. As seen in FIG. 15, the surface follower wheels 124 protrude only slightly beyond the clamshell housing. The axes of rotation of wheels 124 are indicated by line intersections A and B in FIG. 15. Axes A and B correspond to the centers of surface follower wheel axles 178, on which surface follower wheels 124 are respectively mounted (see FIG. 16). Axles 178 are captured by flats in each clamshell 166a, 166b. The separation distance S between axes A and B of the surface follower wheels 124 is indicated in FIG. 15. The surface follower wheel separation distance S determines the resolution of normality measurement.

Figure 17:
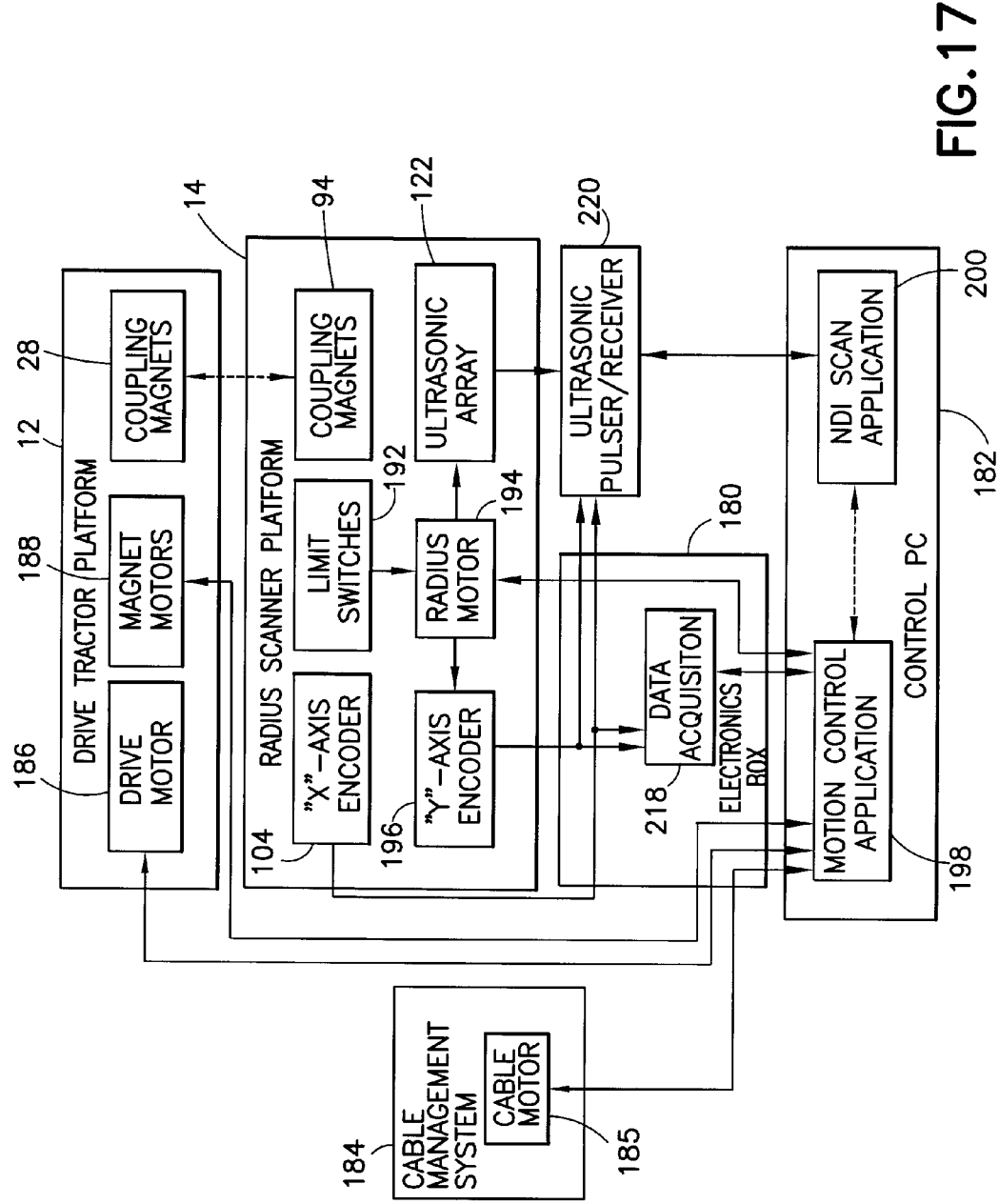
FIG. 17 is a block diagram showing a control system in accordance with one embodiment.

FIG. 17 is a block diagram showing a control system in accordance with one embodiment. The control system comprises a ground-based computer 182 programmed with motion control application software 198 and NDI scan application software 200. The control computer 182 is connected to the drive tractor platform (previously referred to as a "tractor vehicle") 12 and to the radius scanner 14 by flexible electrical cables that connect to an electronics box 180. The electronic box contains the system power supplies and integrates all the scanner control connections and provides an interface between the computer, ultrasonic scanner, drive tractor, and the radius scanner.

The computer 182 may comprise a general-purpose computer programmed with motion control application software 198 comprising respective software modules for controlling drive motor 186 and magnet vertical positioning motors 188 onboard the drive tractor platform 12. The magnet motors 188 displace the tractor coupling magnets 28 as disclosed in U.S. patent application Ser. No. 13/313,267.

Motion control application software 198 also controls a radius motor 194 to produce specified sweeping motions of the sweeper bridge assembly. The sweep angle of the sweeper bridge in both directions is limited by limit switches 192. A Y-axis encoder 196 encodes the angular position of the shaft of radius motor 194, which in turn determines the angular position of the sweeper bridge assembly. As previously described, the sweeping of the bridge assembly is synchronized with the motion of the radius scanner in the X-direction, the position of the radius scanner in the X-direction being indicated by X-axis encoder 104.

In accordance with one embodiment, the encoded data from both encoders 104 and 196 is received by a data acquisition device 218 via a switch and a splitter (not shown) inside the electronic box 180. The data acquisition device 218 also has digital input and output connections that are used for multiple functions within the system. These encoder pulses are also sent to an ultrasonic pulser/receiver 220 (via the aforementioned switch and splitter), which sends those encoder pulses to the NDI scan software 200. The NDI scanning software application 200 uses these pulses to position the scan data in the proper location.

The computer 182 hosts ultrasonic data acquisition and display software that controls the ultrasonic pulser/receiver 220. The ultrasonic pulser/receiver 220 in turn sends pulses to and receives return signals from the ultrasonic transducer array 122. The NDI scan application software 200 controls all details of the scan data and the display of data. The pulser/receiver 220 correlates the acquired ultrasonic data with position information received from the X- and Y-axis encoders 104, 196.

The motion control application software 198 also controls a motor 185 of a cable management system 184. When multiple scanners are operated, there are several cables that need to accompany the scanner and the tractor down the length of the box being inspected. The cable management system 184 consists of two sets of motorized wheels that grip the cables. The cable motor 185 is under computer control, which synchronizes the cables with the movement of the active trailer and the tractor, extending or retracting the cables as appropriate.

In the scanning system described above, the sweeper rotates the plane of the slides through the sweep angle, and the spring-loaded sensor position adjustment subassembly (including the bridge and bridge towers) pushes the topple pivots as close as possible to the part surface, where the follower wheels "topple" the sensor to match the local surface normal. The topple pivot axis must be as close as possible to the surface in order to minimize the location error. Note that if extreme precision were required, an encoder could be incorporated into the topple axis, and this error reported to the controller.

In the particular implementation disclosed above, a long sensor is held in place by two mirror-image follower mechanisms, one on each end of the sensor, which are each driven around the same sweep angle so as to minimize any torque-derived forces along the length of the sensor. The bridge structure connects the two mirrored sides together and eliminates any potential torque between the two sweep pivots.

The toppler keeps the ultrasonic array pointed along the normal to the surface because it is riding on two pairs of bearings that are separated by a small distance (in the plane perpendicular to the X direction of travel). It also may adjust as needed, allowing the topple axis to tilt with respect to the sweep axis, because the two linear slides on each end have enough play that they can "rack" a small amount. The sensor array is rigid. These two effects keep the sensor array normal to the surface, both along the direction of travel and along the direction of sweep, within the limits of the bearing spacings. Because not all four surface follower wheels may be in contact at any given time; the normality of the sensor is a "best average" of the local surface variation.

The implementation disclosed above tracks the surface in a plane perpendicular to the web/flange while holding the array fixed along its length. In accordance with an alternative approach, the array follows the surface both along a plane perpendicular to the web/flange and along X. Only the plane that sweeps around the circumference of the fillet is fixed. This might improve the quality of data produced from longer arrays. Also, it might allow the cable to come up from the array, which would be required if a greater number of array elements were used. By increasing the array length, the inspection time could potentially be reduced.

While various embodiments have been described, it will be understood by those skilled in the art that various changes may be made and equivalents may be substituted for elements thereof without departing from the scope of the teachings herein. For example, a sensor position adjustment subassembly could be designed to translate relative to a bridge assembly, in which case the bridge assembly would sweep but not translate. In addition, many modifications may be made to adapt a particular situation to the teachings herein without departing from the scope thereof. Therefore it is intended that scope of the claims set forth hereinafter not be limited to the disclosed embodiments.

As used in the claims, the term "linear motion guide half" means a structure having a straight surface that guides a contacting surface of another linear motion guide half to move linearly during relative motion of the two halves. More specifically, the term "linear motion guide half" includes, but is not limited to, the male and female slide halves described above.

Furthermore, the method claims set forth hereinafter should not be construed to require that the steps recited therein be performed in alphabetical order or in the order in which they are recited.

The invention claimed is:

1. A scanning system comprising:
a probe body;
a plurality of wheels rotatably mounted to said probe body in a configuration that enables said probe body to move along a radius that connects a flange to a web when first wheels of said plurality of wheels are in contact with the flange and second wheels of said plurality of wheels are in contact with the web;
a sweeper which is rotatably coupled to said probe body so that a sweep axis of said sweeper will be generally parallel to the radius when said first wheels are in contact with the flange and said second wheels are in contact with the web, wherein said sweeper comprises:
first and second sweep drive axles aligned with said sweep axis and rotatably coupled to said probe body;
first and second sweep drive flanges respectively affixed to the first and second sweep drive axles;
a sensor position adjustment subassembly which is translatably mounted to said first and second sweep drive flanges so that a direction of translation of said sensor position adjustment subassembly is transverse to said first and second sweep drive axles, wherein said sensor position adjustment subassembly comprises a toppler that is rotatable about a topple pivot axis that is generally parallel to said sweep axis; and
a sensor that is held by said toppler,
wherein said sensor pivots about said topple pivot axis when said toppler pivots, said toppler translates in said direction of translation when said sensor position adjustment subassembly translates, and said sensor position adjustment subassembly pivots about said sweep axis when said sweeper pivots.

2. The system as recited in claim 1, wherein said sensor comprises a linear ultrasonic transducer array disposed parallel to said sweep axis.

3. The system as recited in claim 1, wherein:
said sensor position adjustment subassembly comprises first and second bridge towers which are translatable relative to said first and second sweep drive flanges in said direction of translation, and a bridge connecting said first and second bridge towers.

4. The system as recited in claim 3, wherein said sensor position adjustment subassembly further comprises first and second toppler pivot axles, said toppler comprises first and second toppler pivot bearings, and respective first portions of said first and second toppler pivot axles are respectively seated in said first and second toppler pivot bearings.

5. The system as recited in claim 3, wherein said first sweep drive flange comprises a first linear motion guide half, and said second sweep drive flange comprises a second linear motion guide half, said sensor position adjustment subassembly further comprising third and fourth linear motion guide halves respectively attached to said first and second bridge towers and respectively translatably coupled to said first and second linear motion guide halves for guiding said sensor position adjustment subassembly to translate in said direction of translation.

6. The system as recited in claim 1, further comprising:
a first motor mounted to said probe body and mechanically coupled to said sweeper, said first motor driving pivoting of said sweeper when actuated;
a second motor mounted to said probe body and mechanically coupled to at least one of said plurality of wheels, said second motor driving movement of said probe body when actuated; and
a motor controller configured to control said first and second motors to operate in a synchronized manner such that a speed of said probe body depends on a length of said sensor and a cycle rate and sweep angle range of said sweeper.

7. The system as recited in claim 6, wherein said motor controller is configured to control said first and second motors so that said sweeper oscillates about said sweep axis while said probe body moves.

8. The system as recited in claim 3, wherein said sensor comprises a linear ultrasonic transducer array disposed parallel to said sweep axis.

9. The system as recited in claim 3, further comprising:
a first motor mounted to said probe body and mechanically coupled to said sweeper, said first motor driving pivoting of said sweeper when actuated;
a second motor mounted to said probe body and mechanically coupled to at least one of said plurality of wheels, said second motor driving movement of said probe body when actuated; and
a motor controller configured to control said first and second motors to operate in a synchronized manner such that a speed of said probe body depends on a length of said sensor and a cycle rate and sweep angle range of said sweeper.

10. The system as recited in claim 9, wherein said motor controller is configured to control said first and second motors so that said sweeper oscillates about said sweep axis while said probe body moves.

11. The system as recited in claim 4, wherein said sensor comprises a linear ultrasonic transducer array disposed parallel to said sweep axis.

12. The system as recited in claim 4, further comprising:
a first motor mounted to said probe body and mechanically coupled to said sweeper, said first motor driving pivoting of said sweeper when actuated;
a second motor mounted to said probe body and mechanically coupled to at least one of said plurality of wheels, said second motor driving movement of said probe body when actuated; and
a motor controller configured to control said first and second motors to operate in a synchronized manner such that a speed of said probe body depends on a length of said sensor and a cycle rate and sweep angle range of said sweeper.

13. The system as recited in claim 12, wherein said motor controller is configured to control said first and second motors so that said sweeper oscillates about said sweep axis while said probe body moves.

14. The system as recited in claim 5, wherein said sensor comprises a linear ultrasonic transducer array disposed parallel to said sweep axis.

15. The system as recited in claim 5, further comprising:
- a first motor mounted to said probe body and mechanically coupled to said sweeper, said first motor driving pivoting of said sweeper when actuated;
- a second motor mounted to said probe body and mechanically coupled to at least one of said plurality of wheels, said second motor driving movement of said probe body when actuated; and
- a motor controller configured to control said first and second motors to operate in a synchronized manner such that a speed of said probe body depends on a length of said sensor and a cycle rate and sweep angle range of said sweeper.

16. The system as recited in claim 15, wherein said motor controller is configured to control said first and second motors so that said sweeper oscillates about said sweep axis while said probe body moves.

17. The system as recited in claim 1, further comprising a spring that exerts a spring force on the sensor position adjustment subassembly that urges the sensor position adjustment subassembly to extend until said sensor is in contact with the radius when said first wheels are in contact with the flange and said second wheels are in contact with the web.

18. The system as recited in claim 3, further comprising first and second springs, wherein one end of said first spring is coupled to a first spring post attached to said first sweep drive axle and another end of said first spring is coupled to a second spring post attached to said sensor position adjustment subassembly, while one end of said second spring is coupled to a third spring post attached to said second sweep drive axle and another end of said second spring is coupled to a fourth spring post attached to said sensor position adjustment subassembly.

* * * * *